United States Patent [19]

Himmler

[11] Patent Number: 5,049,693

[45] Date of Patent: Sep. 17, 1991

[54] PROCESS FOR THE SELECTIVE HYDROGENATION OF OLEFINS CONTAINING NITRILE GROUPS

[75] Inventor: Thomas Himmler, Cologne, Fed. Rep. of Germany

[73] Assignee: Bayer Aktiengesellschaft, Leverkusen, Fed. Rep. of Germany

[21] Appl. No.: 539,570

[22] Filed: Jun. 18, 1990

[30] Foreign Application Priority Data

Jun. 29, 1989 [DE] Fed. Rep. of Germany ....... 3921263

[51] Int. Cl.$^5$ ............................................ C07C 253/30
[52] U.S. Cl. .................................. 558/467; 558/431; 558/459; 525/338; 525/339
[58] Field of Search ................ 558/459, 431, 467, 434; 525/338, 339

[56] References Cited

U.S. PATENT DOCUMENTS

| | | | |
|---|---|---|---|
| 3,322,815 | 5/1967 | Feldman et al. | 558/459 X |
| 3,700,637 | 10/1972 | Finch, Jr. | 525/339 X |
| 4,362,671 | 12/1982 | Diamond et al. | 558/459 |
| 4,389,348 | 6/1983 | Diamond et al. | 558/459 |
| 4,464,515 | 8/1984 | Rempel et al. | 525/339 X |
| 4,503,196 | 3/1985 | Rempel et al. | 525/338 |
| 4,601,859 | 7/1986 | Galle et al. | 558/459 |
| 4,673,757 | 6/1987 | Fiedler et al. | 558/467 X |
| 4,795,788 | 1/1989 | Himmler et al. | 525/338 |

FOREIGN PATENT DOCUMENTS

| | | |
|---|---|---|
| 0134023 | 3/1985 | European Pat. Off. |
| 0174576 | 3/1986 | European Pat. Off. |
| 0298386 | 1/1989 | European Pat. Off. |
| 3529252 | 2/1987 | Fed. Rep. of Germany |
| 2539132 | 4/1987 | Fed. Rep. of Germany |
| 3540918 | 5/1987 | Fed. Rep. of Germany |

OTHER PUBLICATIONS

Inorganica Chimica Acta, vol. 104, "Platinum Group Metal Chelates Derived from 2-Mercapto, . . . ", pp. L5-L6, (1985).

*Primary Examiner*—Joseph Paul Brust
*Attorney, Agent, or Firm*—Connolly and Hutz

[57] ABSTRACT

The hydrogenation of olefins containing nitrile groups in the homogeneous phase can be carried out particularly successfully using specific ruthenium complexes which are non-sensitive to air and have high catalytic activity.

10 Claims, No Drawings

PROCESS FOR THE SELECTIVE HYDROGENATION OF OLEFINS CONTAINING NITRILE GROUPS

This invention relates to a process for the hydrogenation of compounds containing at least one olefinic C=C double bond and at least one nitrile group per molecule in the presence of ruthenium compounds, the nitrile groups remaining intact.

Processes for the selective hydrogenation of olefins containing nitrile groups (i.e. for the hydrogenation of the C=C double bond with the nitrile bonds intact) are known. In U.S. Pat. No. 3,700,637, rhodium/halogen complex catalysts are recommended for the selective hydrogenation of diene/(meth)acrylonitrile copolymers. The suitability of other metals, such as platinum, ruthenium, iridium, palladium, rhenium, cobalt or copper, homogeneous or heterogeneous, is mentioned.

It is known from DE-PS 2 539 132 that the vinylic and the trans C=C-double bonds of butadiene/acrylonitrile copolymers can be quantitatively hydrogenated with rhodium/halogen complex catalysts providing chlorobenzene is used as solvent while the cis C=C-double bonds and the —C≡N+ triple bonds remain intact; in other solvents, particularly ketones, only low degrees of hydrogenation are obtained.

EP-A 134 023 describes the selective hydrogenation of nitrile rubbers in an aromatic solvent in the presence of tris-(triphenylphosphine)-rhodium(I) halide as catalyst using triphenylphosphine.

U.S. Pat. No. 4,464,515 describes the selective hydrogenation of copolymers of conjugated dienes and copolymerizable monomers in the presence of (i) a monovalent rhodium hydride complex catalyst, (ii) a second ligand and (iii) a solvent for (i), (ii) and the copolymer. U.S. Pat. No. 4,503,196 relates to the same hydrogenation in the absence of the second ligand (ii).

Since the occurrence of rhodium is very limited and since rhodium is used not only in the chemical industry, but predominantly in the electrical industry, in the glass industry and ceramics industry and, of late, particularly in the automotive industry (emission control catalysts), there could be a shortage of this noble metal in the future. Accordingly, it was desirable to develop processes for the selective hydrogenation of olefins containing nitrile groups, more especially processes for the selective hydrogenation of nitrile rubbers, which did not involve the use of rhodium catalysts. Various proposals have also been put forward in this regard:

EP-A 174 576 describes the selective hydrogenation of unsaturated polymers containing nitrile groups using a low molecular weight ketone as solvent and a compound corresponding to the following formula $$RuX\,[(L^1)\,(L^2)_n]\qquad(I)$$

in which
X is hydrogen, halogen
$L^1$ is hydrogen, halogen, optionally substituted cyclopentadienyl,
$L^2$ is a phosphine, bisphosphine or arsine and
n is 1, 2 or 3,
and $[(L^1)\,(L^2)_n]$ is a cyclopentadienyl bisphosphine, as catalyst.

U.S. Pat. No. 4,795,788 describes the selective hydrogenation of unsaturated polymers containing nitrile groups in the presence of a catalyst corresponding to formula I, in which
X is hydrogen, halogen or SnCl$_3$,
$L^1$ is optionally substituted indenyl,
$L^2$ is phosphine, bisphosphine or
n is 1 or 2.

DE-OS 3 540 918 describes the selective hydrogenation of unsaturated compounds, more particularly the selective hydrogenation of nitrile rubber, in the presence of a catalyst corresponding to the following formula $$RuH_{2n}\,L_{5-n}\qquad(II)$$

in which
L is a phosphine or arsine and
n is 1 or 2.

DE-OS 3 529 252 recommends the selective hydrogenation of unsaturated polymers containing nitrile groups in the presence of a catalyst corresponding to the following formula $$RuH_m\,(R^1COO)_n\,(L_p)\qquad(III)$$

in which
$R^1$ is alkyl, aryl, cycloalkyl or aralkyl,
L is a phosphine or arsine,
m is 0 or 1,
n is 1 or 2 and
p is 2 or 3.

EP-A 298 386 describes the selective hydrogenation of unsaturated copolymers in the presence of various ruthenium carbonyl complexes.

The ruthenium complexes described as hydrogenation catalysts are sensitive to air and/or show relatively poor catalytic activity, so that they have to be used in large quantities.

The problem addressed by the present invention was to provide a process for the selective hydrogenation of olefins containing nitrile groups which did not involve the use of rhodium and which could also be used for the hydrogenation of polymers; the complexes required for this hydrogenation process on the one hand were to be unaffected by air and, on the other hand, were to show high catalytic activity.

It has now surprisingly been found that this problem is successfully solved by hydrogenation in homogeneous phase using ketones as solvent, providing specially selected ruthenium complexes are used as the hydrogenation catalysts.

Accordingly, the present invention relates to a process for the selective hydrogenation of olefins containing nitrile groups with hydrogen in an organic solvent in the presence of a hydrogenation catalyst, characterized in that
(i) an aliphatic C$_{3-6}$ ketone and/or a cycloaliphatic C$_{5-6}$ ketone is used as the organic solvent and
(ii) a compound corresponding to the following formula $$RuH_m\,(L^1)_n\,(CO)_p\,(L^2)_q\qquad(IV)$$

in which
X is hydrogen, halogen (fluorine, chlorine, bromine) or SnCl$_3$,
$L^1$ is an anionic radical corresponding to the following formula

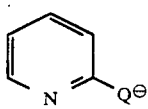 (V)

in which
Q is oxygen, sulfur or NH,
$L^2$ is phosphine, bisphosphine or arsine,
m is 0, 1 or 2,
n is 1 or 2,
p is 0 or 1 and
q is 1 or 2,
is used as the hydrogenation catalyst.

$L^2$ ligands are, for example, those corresponding to the formulae

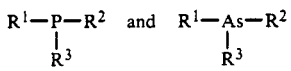

in which $R^1$, $R^2$ and $R^3$ may be the same or different and represent (optionally substituted) alkyl, cycloalkyl, aryl or aralkyl radicals.

Alkyl radicals $R^1$ to $R^3$ are, for example, linear or branched, saturated hydrocarbon radicals containing 1 to 20, preferably 1 to 12 and more preferably 1 to 6 carbon atoms.

Cycloalkyl radicals $R^1$ to $R^3$ are, for example, cyclic, saturated hydrocarbon radicals containing 5 to 12 and preferably 5 to 7 carbon atoms.

Aryl radicals $R^1$ to $R^3$ are, for example, aromatic hydrocarbon radicals from the benzene series containing 6 to 18 and preferably 6 to 12 carbon atoms.

Aralkyl radicals $R^1$ to $R^3$ are, for example, aryl-substituted alkyl radicals which, in the aliphatic part, consist of a linear or branched $C_{1-6}$ hydrocarbon radical and, in the aromatic part, of a radical of the benzene series, preferably phenyl.

The alkyl, cycloalkyl, aryl and aralkyl radicals mentioned above may optionally be substituted by $C_{1-6}$ alkyl, hydroxy, $C_{1-6}$ alkoxy, $C_{1-6}$ carbalkoxy, fluorine or chlorine.

Preferred $L^2$ ligands are phosphine, diethyl phenyl phosphine, tritolyl phosphine, trinaphthyl phosphine, diphenyl phosphine, tributyl phosphine, tris-(trimethoxyphenyl)-phosphines, bis-(trimethylphenyl)-phenyl phosphines, bis-(trimethoxyphenyl)-phenyl phosphines, trimethylphenyl-diphenyl phosphines, trimethoxyphenyldiphenyl phosphines, bis-(dimethoxyphenyl)-phenyl phosphines, dimethylphenyl-diphenyl phosphines, dimethoxyphenyl-diphenyl phosphines, triphenyl arsine, ditolyl Phenyl arsine, tris(4-ethoxy)-arsine, diphenyl-cyclohexyl arsine, dibutylphenyl arsine and diethyl-phenyl arsine.

Other examples of $L^2$ ligands are bisphosphines corresponding to the following formula

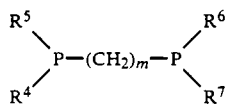

in which m is an integer of 1 to 10 and the substituents $R^4$ to $R^7$ have the same meaning as $R^1$.

Examples of bisphosphines are 1,2-bis-(diphenylphosphino)-ethane, 1,2-bis-(dianisylphosphino)-ethane, preferably 1,3-bis-(diphenylphosphino)-propane and, in particular, 1,4-bis-(diphenylphosphino)-butane.

The preferred ligand L is the radical V in which Q is oxygen.

The particularly preferred catalyst is bis-(2-hydroxypyridinato)-bis-(triphenylphosphane)-ruthenium(II).

The hydrogenation catalysts to be used in accordance with the invention and processes for their production are either known or their production may be carried out analogously to known production processes; V. Alteparmakian, P. Mura, B. G. Olby and S. D. Robinson, Inorg. Chim. Acta 104 (1985) L5.

Olefins containing nitrile groups suitable for the process according to the invention include, for example, acrylonitrile, methacrylonitrile and cyclohex-3-ene nitrile.

Preferred Olefins containing nitrile groups for the process according to the invention are polymers having average molecular weights determined as number averages $\overline{M}_w$ in the range from 500 to 500,000, preferably in the range from 1000 to 200,000 and more preferably in the range from 30,000 to 150,000. The molecular weights $\overline{M}_w$ may be determined by gel permeation chromatography using polystyrene as standard.

Preferred olefinically unsaturated polymers containing nitrile groups include copolymers of 85 to 50% by weight and preferably 82 to 55% by weight of at least one conjugated diene, 15 to 50% by weight and preferably 18 to 45% by weight of at least one unsaturated nitrile and 0 to 10% by weight and preferably 0 to 8% by weight of at least one other monomer copolymerizable with conjugated dienes and unsaturated nitriles.

Suitable conjugated dienes are, for example, 1,3-butadiene, 2-methyl-1,3-butadiene, 2,3-dimethyl-1,3-butadiene and 1,3-pentadiene; suitable unsaturated nitriles are acrylonitrile and methacrylonitrile.

The other monomers may be aromatic vinyl compounds, such as styrene, o-, m- or p-methyl styrene, ethyl styrene, vinyl naphthalene and vinyl pyridine, α,β-unsaturated monocarboxylic acids containing 3 to 5 carbon atoms, such as acrylic acid, methacrylic acid and crotonic acid, and α,β-unsaturated dicarboxylic acids containing 4 to 5 carbon atoms, such as maleic acid, fumaric acid, citraconic acid and itaconic acid, also vinyl chloride, vinylidene chloride, N-methylol acrylamide and vinyl alkyl ethers containing 1 to 4 carbon atoms in the alkyl part.

The most preferred olefinically unsaturated polymers containing nitrile groups are nitrile rubbers having glass transition temperatures below 0° C. and preferably below −10° C. Preferred nitrile rubbers are butadiene/acrylonitrile copolymers containing 5 to 60% by weight and preferably 10 to 50% by weight copolymerized acrylonitrile. They have Mooney viscosities (DIN 53 523) of generally from 10 to 150 and preferably from 25 to 80 (ML 1+4/100° C.).

Both the olefins containing nitrile groups used as starting products and the hydrogenation products produced therefrom should show relatively high solubility in the organic solvent used. Accordingly, preferred organic solvents are acetone, butanone, pentanones, cyclopentanone and cyclohexanone.

The concentration of catalyst (expressed as ruthenium and based on the olefin containing nitrile groups to be hydrogenated) is generally from 10 to 1000 ppm and preferably from 40 to 600 ppm. The concentration of olefin containing nitrile groups, based on the solution as a whole, is generally from 1 to 90% by weight and preferably from 5 to 40% by weight.

The hydrogenation is best carried out at 80° to 200° C., preferably at 100° to 180° C. and more preferably at 120° to 160° C. under a hydrogen pressure of 20 to 350 bar and preferably 30 to 250 bar.

The degrees of hydrogenation (percentage of hydrogenated C=C double bonds, based on the total number of C=C double bonds originally present in the starting product) may be up to 100%. If necessary, however, the hydrogenation reaction may be terminated at an earlier stage. Products having degrees of hydrogenation of more than 80% are preferably produced by the process according to the invention. The degree of hydrogenation may be determined by IR spectroscopy.

After the hydrogenation reaction, the reaction products may be separated from the solution by standard methods, including for example distillation, concentration by evaporation (optionally under reduced pressure), injection of steam and addition of a precipitant (non-solvent). The reaction products may then be dried to remove residual solvent or water.

Where the hydrogenation products are rubbers, they may be vulcanized in the usual way by peroxide or sulfur vulcanization or by radiation crosslinking. By virtue of their excellent resistance to weathering, ozone, oil and hot air in cold climates, these hydrogenated polymers may be used, as already known, for high-quality rubber articles, such as seals, hoses, membranes, for cable insulation and sheathing.

EXAMPLES 1 and 2

The process according to the invention is described with reference by way of example to the hydrogenation of cyclohex-3-ene nitrile:

EXAMPLE 1

A solution of 0.51 mol cyclohex-3-ene nitrile and 0.163 mmol Ru(pyO)$_2$ (PPh$_3$)$_2$ (pyO=C$_5$H$_4$N—2—O$^\Gamma$) ( 0.03 mol-% or 300 ppm Ru) in acetone is introduced under nitrogen into a 0.7 liter stirred autoclave of stainless steel. After a hydrogen pressure of 30 bar has been established, the contents of the autoclave are heated to 130° C., the hydrogen pressure is increased to 90 to 100 bar and is then maintained for 4 hours. After cooling, the autoclave is vented and the reaction solution is analyzed by gas chromatography. The conversion of cyclohex-3-ene nitrile is more than 99%.

EXAMPLE 2

The procedure is as in Example 1, except that Ru(-pyNH)$_2$ (PPh$_3$)$_2$ (pyNH=C$_5$H$_4$N—2—NH$^\theta$) is used as catalyst. The conversion of cyclohex-3-ene nitrile is more than 99%.

EXAMPLES 3 to 6

These Examples describe the hydrogenation of a butadiene/acrylonitrile copolymer:

EXAMPLE 3

0.257 g Ru(pyO)$_2$ (PPh$_3$)$_2$ (=200 ppm Ru) are dissolved in 1.6 kg nitrogen-purged acetone. 160 g of a statistical butadiene/acrylonitrile polymer containing 34.9% by weight copolymerized acrylonitrile and having a Mooney viscosity of 29 (ML 1+4 100° C.) are then dissolved. The resulting solution is transferred to a 3 liter stirred autoclave of stainless steel. After a hydrogen pressure of 80 bar has been established, the contents of the autoclave are heated to 135° C., after which the pressure is increased to 170–180 bar and maintained for 6 hours. The degree of hydrogenation as determined by IR spectroscopy is more than 98%.

EXAMPLE 4

160 g of the statistical butadiene/acrylonitrile copolymer of Example 3 are dissolved in 1.6 kg nitrogen-purged acetone. The resulting solution is transferred to a 3 liter autoclave. After a hydrogen pressure of 40 bar has been established, the contents of the autoclave are heated to 100° C., after which the hydrogen pressure is increased to 100 bar. A solution of 0.386 g Ru(pyO)$_2$ (PPh$_3$)$_2$ ($\doteq$ 300 ppm Ru) in 30 ml chlorobenzene is then introduced into the autoclave under hydrogen excess pressure. The reaction temperature is increased to 135° C. and the pressure to 180 bar. After 4 hours, the degree of hydrogenation is more than 98%.

EXAMPLE 5

The procedure is as in Example 4, except that only 0.257 g Ru(pyO)$_2$ (PPh$_3$)$_2$ ($\doteq$ 200 ppm Ru) is used. The degree of hydrogenation after 6 hours is 80%.

EXAMPLE 6

The procedure is as in Example 4, except that only 0.193 g Ru(pyO)$_2$ (PPh$_3$)$_2$ ($\doteq$ 150 ppm Ru) is used. The degree of hydrogenation after 6 hours is 70%.

I claim:

1. A process for the selective hydrogenation of the carbon double bonds in olefins containing nitrile groups with hydrogen in an organic solvent in the presence of a hydrogenation catalyst under hydrogen pressure of 20 to 350 bar at a temperature from 80° to 200° C., characterized in that
(i) an alkanone containing 3 to 6 carbon atoms or a cycloalkanone containing 5 to 6 carbon atoms is used as the organic solvent and
(ii) a compound corresponding to the following formula

$$RuX_m (L^1)_n (CO)_p (L^2)_q \qquad (IV)$$

in which
X is hydrogen, fluorine, chlorine, bromine or SnCl$_3$,
L$^1$ is an anionic radical corresponding to the following formula

(V)

in which Q is sulfur or NH,
L$^2$ is a ligand corresponding to at least one of the formulae

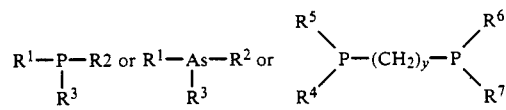

in which R$^1$, R$^2$ and R$^3$ are the same or different and represent linear or branched saturated alkyl radicals containing 1 to 20 carbon atoms, cyclic saturated aliphatic radicals containing 5 to 12 carbon atoms, aromatic hydrocarbon radicals from the benzene series containing 6 to 18 carbon atoms, or aralkyl radicals which, in the aliphatic part, consist of a linear or branched $C_{1-6}$ hydrocarbon radical and, in the aromatic part, of a radical of the benzene series, y is an integer of 1 to 10 and $R^4$ to $R^7$ have the same meaning as $R^1$, m is 0, 1, or 2,
n is 1 or 2,
p is 0 or 1 and
q is 1 or 2,
is used as the hydrogenation catalyst.

2. A process as claimed in claim 1, in which $L^2$ is a triphenyl phosphine.

3. A process as claimed in claim 1, in which p is 0 and q is 2.

4. A process as claimed in claim 1, in which m is 0, n is 2, p is 0 and q is 2.

5. A process as claimed in claim 1, in which acetone or butanone is used as the solvent.

6. A process according to claim 1 wherein $R^1$, $R^2$ and $R^3$ are the same or different and represent linear or branched, saturated alkyl radicals containing 1 to 12 carbon atoms.

7. A process according to claim 6 wherein the alkyl radicals contain 1 to 6 carbon atoms.

8. A process according to claim 1 wherein $R^1$, $R^2$ and $R^3$ are the same or different and represent cyclic, saturated aliphatic radicals containing 5 to 7 carbon atoms.

9. A process according to claim 1 wherein $R^1$, $R^2$ and $R^3$ are the same or different and represent aromatic hydrocarbon radicals from the benzene series containing 6 to 12 carbon atoms.

10. A process according to claim 1 wherein $R^1$, $R^2$ and $R^3$ are the same or different and represent aralkyl radicals which, in the aliphatic part, consist of a linear or branched $C_{1-6}$ hydrocarbon radical and, in the aromatic part, consists of phenyl.

* * * * *